(12) United States Patent
Flanders et al.

(10) Patent No.: US 7,564,548 B2
(45) Date of Patent: Jul. 21, 2009

(54) LOW PIXEL COUNT TUNABLE LASER RAMAN SPECTROSCOPY SYSTEM AND METHOD

(75) Inventors: Dale C. Flanders, Lexington, MA (US); Petros Kotidis, Framingham, MA (US); Xiaomei Wang, Winchester, MA (US)

(73) Assignee: Axsun Technologies, Inc., Billerica, MA (US)

( * ) Notice: Subject to any disclaimer, the term of this patent is extended or adjusted under 35 U.S.C. 154(b) by 23 days.

(21) Appl. No.: 11/692,625

(22) Filed: Mar. 28, 2007

(65) Prior Publication Data

US 2008/0030726 A1 Feb. 7, 2008

Related U.S. Application Data

(60) Provisional application No. 60/743,861, filed on Mar. 28, 2006, provisional application No. 60/867,858, filed on Nov. 30, 2006.

(51) Int. Cl.
*G01J 3/44* (2006.01)
*G01N 21/65* (2006.01)
(52) U.S. Cl. .......................... 356/301; 356/71
(58) Field of Classification Search .................. 356/301
See application file for complete search history.

(56) References Cited

U.S. PATENT DOCUMENTS

| 2002/0031163 | A1 | 3/2002 | Tedesco |
| 2005/0007583 | A1 | 1/2005 | DiFoggio |
| 2005/0105084 | A1 | 5/2005 | Wang et al. |
| 2005/0264808 | A1* | 12/2005 | Wang ........................ 356/328 |
| 2006/0132782 | A1 | 6/2006 | Flanders et al. |
| 2006/0147148 | A1 | 7/2006 | Wang et al. |
| 2006/0176478 | A1 | 8/2006 | Clarke et al. |
| 2006/0187457 | A1 | 8/2006 | Atia et al. |
| 2006/0215713 | A1 | 9/2006 | Flanders et al. |
| 2007/0195320 | A1 | 8/2007 | Sriram et al. |

FOREIGN PATENT DOCUMENTS

EP 0974811 A1 1/2000

OTHER PUBLICATIONS

U.S. Appl. No. 11/357,899, filed on Feb. 17, 2006 by Sriram et al.
PCT International Search Report from International application No. PCT/US2007/065361, mailed Oct. 8, 2007.
International Preliminary Report on Patentability dated Oct. 9, 2008, from International Application No. PCT/US2007/065361, filed on Mar. 28, 2007.

* cited by examiner

*Primary Examiner*—F. L Evans
(74) *Attorney, Agent, or Firm*—Houston Eliseeva, LLP

(57) ABSTRACT

A Raman system uses a semiconductor tunable laser subsystem to generate a tunable signal that is tuned over a scan band of greater than 50 nanometers. A probe system transmits the tunable signal to a sample. Finally a detector system comprises a bandpass filter for filtering a Raman signal from the sample generated by the tunable signal, and a detector for detecting the filtered Raman signal.

37 Claims, 3 Drawing Sheets

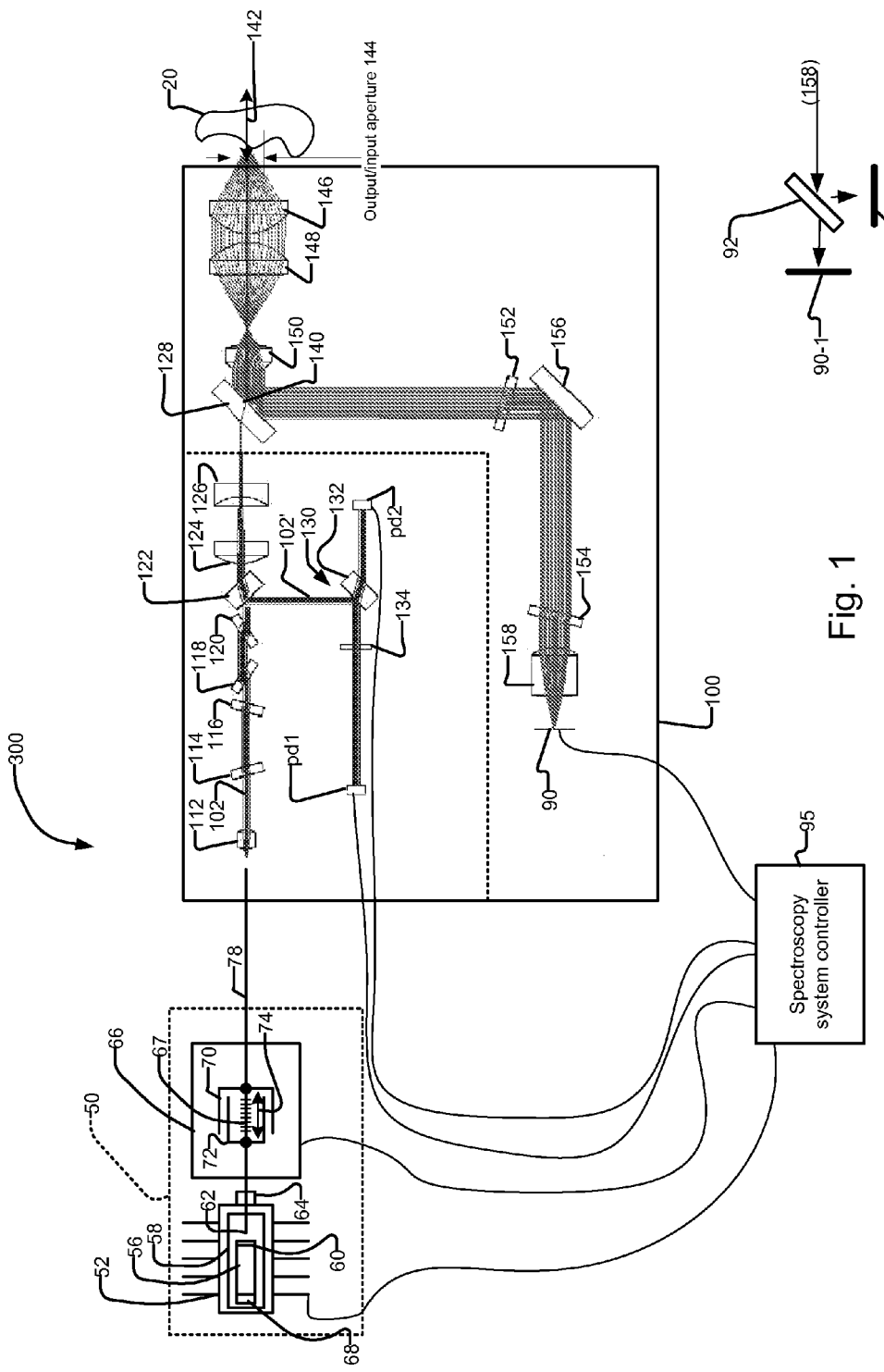

LOW PIXEL COUNT TUNABLE LASER RAMAN SPECTROSCOPY SYSTEM AND METHOD

RELATED APPLICATIONS

This application claims the benefit under 35 U.S.C. 119(e) of U.S. Provisional Application Nos. 60/743,861, filed on Mar. 28, 2006 and 60/867,858 filed on Nov. 30, 2006 both of which are incorporated herein by reference in their entirety.

BACKGROUND OF THE INVENTION

Raman spectroscopy, a vibrational spectroscopy technique, is an analytic tool for probing molecular and biological structures and understanding the chemical properties. The highly structured, information-rich Raman spectra, like fingerprints, can be used to identify wide range of chemical compounds and materials. For example, this technique has been used to identify hazardous materials and contraband drugs, and for monitoring chemical manufacturing processes and for pharmaceutical drug development.

Raman spectroscopy has several distinct advantages over other analytical tools such as infrared (IR) spectroscopy and gas/liquid chromatography (GC/LC). The most important advantages include the fact that it: 1) is a non-invasive and non-destructive technique, 2) can avoid sample preparation, and 3) can be used for aqueous samples. In comparison, GC/LC can only be used for liquid and gas materials, and it utilizes a destructive sampling technique by extracting samples that are sent through separation columns. Furthermore, the sampling and identification time of the GC/LC method is typically several minutes, which is not suitable for many applications.

Infrared (IR) spectroscopy provides similarly information-rich spectra like Raman spectra by probing the vibrational states of molecules. Its big drawback, however, is that IR spectroscopy cannot be effectively used for aqueous samples due to strong water absorptions; even for many other materials it requires preparation of thin samples. These comparisons make the Raman spectroscopy the preferred technique for many substance identification or diagnostic applications that require field autonomous, non-contact, non-invasive or non-destructive characteristics and can identify a diverse range of materials.

SUMMARY OF THE INVENTION

Recent advances in the development of compact dispersive Raman spectrometers have presented the opportunity to deploy this technique into the field, broadening its use in new industrial, security, and military applications.

Nevertheless, the state-of-the-art instruments are complex and thus can not be provided at low cost and in a small form factor. In many cases, however, new applications are critically enabled by the recent advancements in nano-materials, nano-technologies and other specialty materials, including surface enhanced Raman spectroscopy (SERS). Thus, the potentials of these new applications can only be realized with truly miniature and low-cost Raman spectrometers, such as readers.

The present invention concerns a Raman spectrometer, that can be deployed as a reader, for example, and can be used for substance or taggant identification applications. The spectrometer utilizes on semiconductor tunable laser, which in combination with a low pixel count detector or even a single pixel detector, has the potential to have a significantly reduced cost and/or complexity relative to current spectrometers.

In general according to one aspect, the invention features a Raman system that uses a semiconductor tunable laser subsystem to generate a tunable signal that is tuned over a scan band of greater than 50 nanometers. A probe system transmits the tunable signal to a sample. Finally a detector system comprises a bandpass filter for isolating a Raman signal from the sample that was generated by the tunable signal, and a detector for detecting the filtered Raman signal.

In general according to another aspect, the invention features a method for obtaining and using a Raman response. This method includes generating a tunable signal with a semiconductor tunable laser and varying a wavelength of the tunable signal over a scan band of greater than 50 nanometers. The tunable signal is transmitted to a sample, and a returning Raman signal from the sample is bandpass filtered. The Raman signal is then detected and analyzed.

In general according to still another aspect, the invention features a Raman analysis system that comprises a semiconductor tunable laser subsystem for generating a tunable signal that is tuned over a scan band and a detector system, comprising a bandpass filter for filtering a Raman signal from the sample generated by the tunable signal and a detector for detecting the filtered Raman signal. A Raman sample is also provided that generates the Raman signal from the tunable signal.

In different embodiments, the Raman signal from the Raman sample is used to determine an authenticity of an article with which the Raman sample is associated.

In other examples, the Raman sample is in communication with a body of a user of the system.

Preferably, a wireless interface is used to transmit Raman information gathered from the sample to a remote host computer.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a schematic view of a Raman spectroscopy system according to an embodiment of the present invention;

FIG. 1a shows different implementation of the system detector according to another embodiment of the invention;

DETAILED DESCRIPTION OF THE PREFERRED EMBODIMENTS

Figures 2A, 2B:
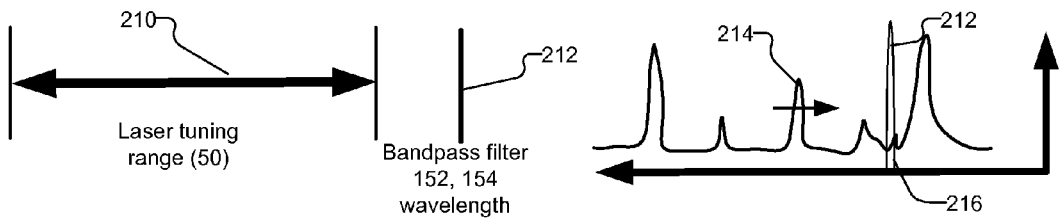
FIGS. 2a-2d are schematic plots showing a relationship between a scan band of a tunable laser subsystem, notch filter wavelength, and an exemplary Raman spectrum, also shown is an embodiment of a laser scanning process.

FIG. 1 shows a Raman spectroscopy system 300, which has been constructed according to the principles of the present invention.

Specifically, it comprises a semiconductor tunable laser subsystem 50, which produces a tunable excitation signal that is tuned over an excitation spectral band. The tunable laser subsystem 50 comprises a semiconductor diode module 52. In the illustrated example, this module 52 is a hermetic package such as a butterfly hermetic package. The diode laser module 52 holds a semiconductor gain element 56. In the present embodiment, this gain element 56 is a semiconductor optical amplifier, and specifically, a reflective semiconductor optical amplifier. These semiconductor reflective optical amplifiers 56 comprise a reflective back facet 68 and an antireflection coated (AR) coated front facet 60. They are useful in the construction of external cavity tunable semiconductor lasers.

In the illustrated embodiment, the external cavity tunable laser configuration is provided by a wavelength tunable element module 66, which provides tunable narrow band feedback into the semiconductor gain element 56. In one embodiment, this is a Bragg grating tuning system. Specifically, it comprises a fiber Bragg grating 67 that is mechanically stretched by a stretcher system 74. Specifically, a first half of the stretcher 70 and a second half of the stretcher 72 are moved toward and away from each other by a mechanical stretching system indicated by arrow 74.

In a different embodiment, the wavelength tunable element 66 is integrated into the hermetic package 52 on the same optical bench 58 as the gain element 56. Examples of integrated tunable diode laser systems are disclosed in United States Patent Application Publ. No. 20060215713, filed on Jun. 22, 2005, by Flanders, et al., which is in incorporated herein by this reference in its entirety. Thus, in other embodiments, one of the integrated laser systems with the tilted resonator tuning element as described in US Pat. Appl. Publ. No. 20060215713 is used as the tunable laser subsystem 50, replacing the subsystem illustrated in FIG. 1.

An optical fiber pigtail 78 transmits the tunable excitation signal from the semiconductor tunable laser subsystem 50 to the probe subsystem 100. In the preferred embodiment, the fiber pigtail 78 is polarization controlling fiber that controls the polarization of the light transmitted through it. Specifically, polarization controlling fiber is used between the gain element 56 and the grating 67 and between the grating and the probe subsystem 100. In the preferred embodiment, it is polarization maintaining fiber, although other polarization controlling systems could be used such as polarization stripping systems or polarizing fiber.

The light from the semiconductor chip 56 is coupled into the fiber pigtail 78 via a fiber facet 62. This fiber goes through the hermetic package 52 via a fiber feedthrough 64 in one example.

In other embodiments, the tunable laser subsystem 50 is free space, i.e., directly coupled, to the probe system 100 in embodiments in which the integrated tunable diode laser system is used.

In one example, the probe subsystem is based on a probe described in U.S. patent application Ser. No. 11/357,899, filed Feb. 17, 2006, by Sriram, et al. which is incorporated herein by this reference in its entirety. However, the light collection path is different since one or more notch filters are used in the present invention rather than the broader passband excitation light filters used in this previous system.

In more detail, the probe subsystem 100 comprises a first collimating lens 112. This receives the excitation signal from the fiber pigtail 78 or traversing free space from the laser subsystem 50 and forms a collimated beam from the typically diverging beam. The excitation signal 102 is preferably filtered to remove amplified spontaneous emission—a spectrally continuous emission from the semiconductor laser that is broadband in spectrum. In the preferred embodiment, two spectral notch or bandpass filters are provided as spontaneous emission filters 114 and 116 which attenuation light outside the scan band of the tunable laser subsystem 50. These suppress the ASE emission by reflecting any light that is outside this scan band of the excitation signal 102.

The probe subsystem 100 also preferably provides for polarization filtering of the excitation signal 102. In a preferred embodiment, two polarizers 118 and 120 are used. These filters 118, 120 ensure that the excitation signal 102 has substantially only a single polarization. The single polarization of the excitation signal is important because of polarization dependent loss (PDL) in the taps and other polarization changes due to ambient changes, for example, lead to tracking errors of the wavelength and/or an amplitude of the excitation signal 102 that can not be effectively addressed with calibration.

A partially reflective excitation mirror 122 is provided in the path of the excitation signal 102. This reflects a portion 102' of the excitation signal to a wavelength/amplitude reference system 130.

The wavelength/amplitude reference system 130 in the preferred embodiment detects both the instantaneous wavelength of the excitation signal 102 along with its amplitude or power. In the current implementation, this is achieved by using a partially reflective reference mirror 132. This reflects the excitation signal received by the wavelength reference system 130 through a wavelength reference element 134. In the preferred embodiment, this is a fixed wavelength etalon. A slope filter could also be used. As such, the reference has an Airy transmission function with the etalon to pass light at specific wavelengths and reflect wavelengths outside those ranges. The light transmitted through the wavelength reference element 134 is detected by a first photodetector pd1. Light reflected by the wavelength element 134 is transmitted back through the partially reflective reference mirror 132 to a second photodiode pd2.

The excitation signal 102 that is not reflected by the partially reflective excitation mirror 122 passes through excitation optics. Specifically, the excitation optics comprises a focusing lens 124 and a diverging lens or concave lens 126. This has the effect of focusing the excitation signal down to a small diameter and increasing its working distance. Specifically, in the illustrated embodiment, a separation mirror device 128 is used. This is a mirror that is angled relative to the axis of the excitation signal 102 and a collection axis 142 that passes through an input/output aperture 144 to the sample 20. The angled mirror 128 has a pinhole aperture 140 in its reflective coating. The excitation signal 102 passes though mirror aperture 140 to the output aperture 144. This configuration has advantages in easing alignment between the excitation and collection paths.

The sample 20, responding to the excitation signal 102 produces a Raman response. This is collected by a high numerical aperture (NA) system. Specifically, two focusing lenses 146 and 148 are used to collect the light from the sample 20 while improving the working distance. They are transmitted to a third focusing lens 150 that collimates the light from the sample 20. This light is then directed by mirror 125 to be filtered by a first notch filter 152 and a second notch filter 154. Each of these filters stops or blocks all but a single passband. A fold mirror 156 is used to bend the light from the sample to a focusing lens 158 that couples the light to a detector 90.

A spectroscopy system controller 95 uses a detector 90 to detect the light returning from the sample 20 within the notch passband of the filters 152, 154. Thus, in conjunction with the tuning of the tunable laser subsystem 50, the Raman spectral response of the sample is resolved.

In a preferred embodiment the detector system is a low pixel count system. In a current embodiment, only a single detector is used. Generally less than 5 detectors are used. If multiple detectors are used, then a wavelength dispersive element is located between the detectors and the lens 158.

The spectroscopy system controller 95 controls the power to the diode semiconductor chip 56 and the tuner 66 to thereby generate the tunable excitation signal 102 and scan this signal over the scan range or band. In the preferred embodiment, the scan band is greater than 50 nanometers, with the tunable signal being scanned continuously or semi-continuously through the band. In some other embodiments, the scan band is wider, such as about 100 to 150 nanometers, or 200 nanometers, and possibly up to 300 nanometers, or more. Controller 95 further monitors the response of the first photodiode pd1 and the second photodiode pd2 in order to calculate both the wavelength and the amplitude of the excitation signal 102. With this information, including the response of the detector 90, the spectroscopy controller determines the Raman response of the sample 20.

In one example, the spectroscopy system controller 95 is implemented in electronics including possibly a field programmable gate array and a signal processor. This connects to a host computer, such as a standard personal computer. The spectroscopy system controller 95 loads the Raman spectral information to the host.

FIG. 1a shows a second embodiment in which the single detector 90 is replaced with a detector system. Specifically, a dichrotic filter 92 is added. The dichroic filter 92 is configured to have a filtering function edge within the spectral passband of passband filters 152, 154. In one example, the edge of filter 92 is spectrally centered in the passband of filters 152, 154. Thus, light within the passband of filters 152, 154 is divided between an upper wavelength range and a lower wavelength range. Specifically, in one example, light within the passband of filters 152, 154 and having a longer wavelength than the edge of filter 92 is transmitted to detector 90-1 through filter 92, and light within the passband of filters 152, 154 and having a shorter wavelength than the edge of filter 92 is reflected by the filter 92 to detector 90-2. This embodiment can be used to improve resolution.

Referring to FIG. 2a, at any given laser wavelength within the tuning range 210 of the tunable laser system 50, the broadband Raman signal is collected by the probe 100 and filtered by a fixed narrow bandpass filter(s) 152, 154 that apply the notch filter function 212. The notch filtered light is focused on the detector 90. The difference between the instantaneous frequency of the laser 50 and the bandpass filter wavelength 212 is the Raman shift frequency and the signal level detected by detector 90 is the response at that shift frequency. As the laser wavelength is scanned through its full tuning range of 100 to 300 nanometers, the full Raman spectrum is obtained by the controller 95.

FIG. 2b illustrates the relationship between the Raman spectrum 214 and the passband 212. Specifically, the tuning of the laser 50 over its scan band 50 causes a resulting spectral shift in the Raman spectrum 214 so that the Raman spectrum is "pulled through" the stationary, fixed filter function 212. Thus by monitoring the time response of the detector 90, the controller 95 is able to construct the spectral characteristics of the Raman signal 214.

Figures 2C, 2D:
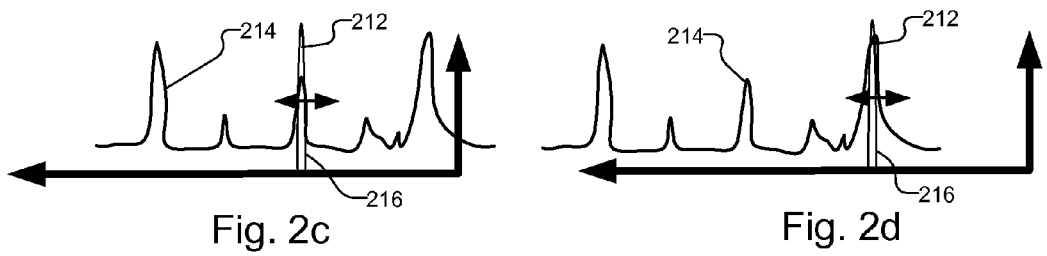

FIGS. 2c and 2d illustrate a modified scanning technique for improving the signal to noise ratio for the peak information of the Raman spectrum 214. Specifically, the laser 50 is wavelength scanned within subband of scan band, such as dithered, at Raman shift frequencies where peak information is found or expected based on assumption concerning the Raman response of the sample. For example, the laser 50 is wavelength dithered so that a first peak in the Raman spectrum is dithered under the passband 216 as shown in FIG. 2c, then the wavelength of the laser 50 hops so that a second peak at a second subband is dithered under the passband 216, as shown in FIG. 2d.

Figure 2E:
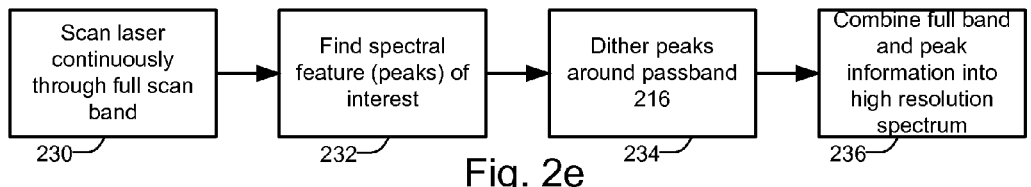
FIG. 2e is a flow diagram illustrating an embodiment of the laser scanning spectral analysis process of the present invention.

FIG. 2e shows one scanning method. First in step 230, the laser 50 is scanned over the entire scan band. During this scan, a low resolution Raman spectrum is accumulated by the controller 95. The controller 95 determines the approximate spectral locations of spectral features, such as peaks, that are of interest in step 232. Often, the controller will spectrally locate the regions of the Raman spectrum that are most useful in characterizing the sample. In some implementations, the controller uses a library of stored spectrums to determine the location of the features of interest. The controller 95 then controls the wavelength of the tunable laser 50 to scan in subbands of the scan band so that those features of interest are dithered around the passband 212. This allows the controller 95 to create localized high resolution information for the Raman spectrum 214 in step 234. Finally, in step 236, the spectral information of the original low resolution scan is combined with the localized high resolution information to create a composite spectrum that is used to analyze the sample 20.

Figure 3:
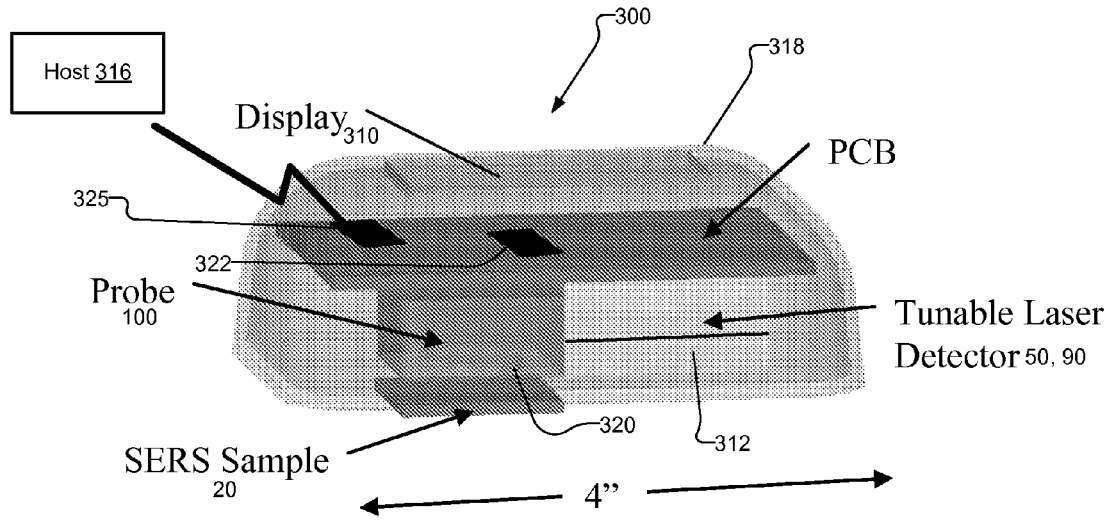
FIG. 3 is a scale perspective view of a Raman spectroscopy system according to an embodiment of the present invention.

FIG. 3 illustrates an exemplary implementation of the Raman spectroscopy system 300. The controller 95 is located on the printed circuit board PCB installed within a housing 318 having an optical port 320. In one example, the housing is small, less than 6 inches long or about 4 inches, and less than 4 inches in height and depth.

Installed on the board PCB is the tunable laser and detector 50, 90. In one example the detector 90 is located in a common hermetic package with the laser system 50 so that a single thermoelectric cooler 312 is used to provide temperature control for both subsystems.

The controller 95 with embedded software handles data acquisition and processing, controls the laser 50 and detector 90 operations including thermal management, e.g., thermoelectric cooler 312, controls and manages user-interface hardware, software and communication as well as the power supply 322. The embedded firmware also performs autonomous substance identification by comparing the resolved spectrum against the built-in library. The identification results will be displayed and reported on user-interface/display device 310, operated by the controller, or transmitted to database management system via defined communication interface. Alternatively, the identification results or the raw spectrum is wirelessly transmitted to a remote host 316 via a wireless interface 325, including an antenna, that is controlled by the controller 95, in still another embodiment.

In one application, the sample 20 includes surface enhanced Raman spectroscopy (SERS) features. SERS has been used for sensitive and selective molecular detection and study. The enhancement factors by the interactions of the nano-surface-structure with analyte can range from $10^6$ to $10^{12}$, depending on the properties of the nanostructures and their fabrication methods. Until recently, the reproducibility of the SERS substrates has hindered the scaling of this technique beyond the laboratory applications. However, recent advancement in nanofabrication has made real-world sensing applications possible for SERS. Technologies such as lithography and colloidal self-assembly process have produced SERS substrates with precisely controlled properties with commercially viable manufacturing processes.

The combination of commercially viable SERS substrates with cost-effective, miniature SERS reader has diverse range of applications, including biomedical diagnostics, biological and chemical agent detection, drug analysis, explosives detection, among others.

Specific examples include the deployment of Raman system 300 with a tailored SERS sample 20 affixed to housing 318, opposite port 320. This is used in one example as a Personal Health Monitor by monitoring the SERS sample for changes. This is a palm-size wearable Raman reader with integrated target-specific SERS strips to (a) determine potential health problems via monitoring critical biomarkers using interstitial fluid, saliva, sweat, tears and/or potentially blood and urine under distressed conditions, e.g. battlefield operations, (b) identify potentially hazardous substances in the field, (c) authenticate identifications using embedded SERS or organic taggants for objects such as military documents.

In another specific example, the system 300 is deployed as a virus detector. This is a palm-size Raman system 300 with specially designed SERS strips 20 that provide field, on the spot determination of viruses in blood or other bodily fluids. Such device is particularly useful in under-developed countries, where medical infrastructure is non-existent and major epidemics, such as AIDS (HIV virus), are widely spread. A low-cost Raman device 300 with built-in SERS strips 20 eliminates the need for elaborate laboratory tests and the potential for erroneous readings—a common problem with today's low performance field devices.

In another application, the spectroscopy system 300 is used in other battlefield applications. The safety of the military personnel, particularly when the biological agents and toxic chemical materials are concerned, is extremely important. The ability of the present system to provide remote sensing of potentially hazardous substances is enabled by the wireless link to the host 316. In this application, the semi-disposable (reusable) sensor system 300 are placed (or thrown) in the area of suspect. The autonomous, miniature, and rugged sensor device detects and identifies the suspect material. Via wireless communication, it transmits and reports results to the military personnel operating the host 316.

Figure 4:
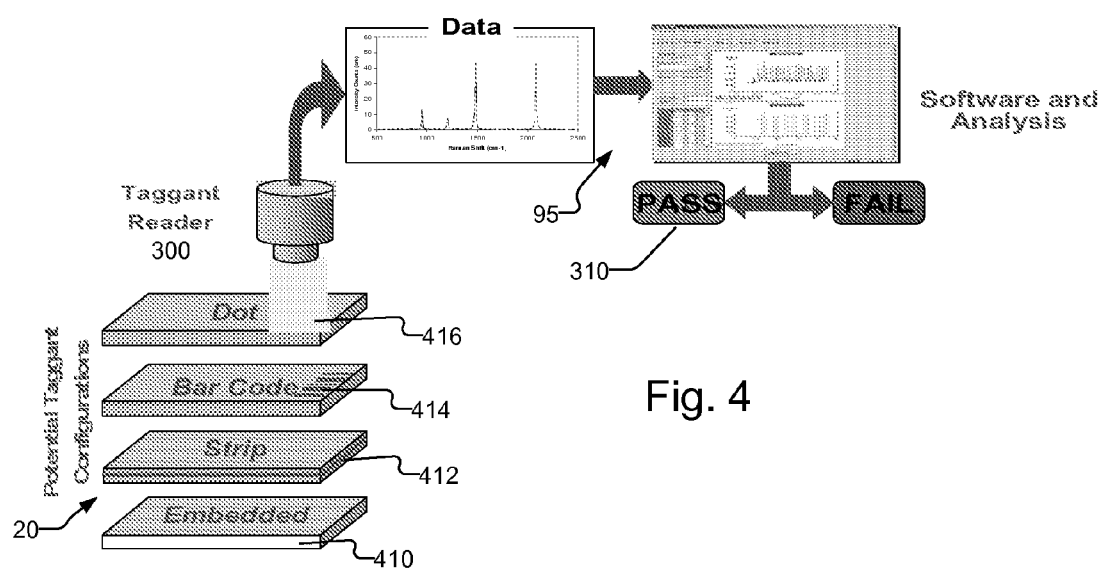
FIG. 4 is a schematic diagram illustrating Raman reader applications for the Raman spectroscopy system.

FIG. 4 illustrates the deployment of the Raman system 300 as a taggant reader in a supply chain, for example.

Samples 20 including Raman taggants are use to mark individual goods or containers (pallets) of goods. In various examples, the taggants 410 are incorporated into the goods packaging or pallets, as a strip on the goods 412, into a bar code label or the ink of the barcode 414 or a dot 416 on the goods themselves. The Raman system 300 is used to read the taggant samples 20. Its controller then analyses 95 and issues a pass/fail or genuine/counterfeit decision via its interface 310.

In one specific example, the taggants 410, 412, 414, 416 and Raman system 300 are used as part of an incoming material inspection system. As part of a company's supply chain system, the Raman system 300 is deployed as a taggant reader to read taggants on incoming material, such as chemicals in a pharmaceutical manufacturing plant. The information read from the taggants is transferred to the supply chain system, which verifies that the taggants and the associated goods are authentic by comparing the taggant spectral signature and information read from the incoming goods with taggant information transmitted from the supply chain management system of the apparent manufacturer or supplier of the goods. In this way, the authenticity of the goods is verified, or not.

These taggants 410, 412, 414, 416, are special complex polymers, which cannot be obtained on the open market, in one implementation. There are a large number of molecule classes and mixtures that can be used for the taggant manufacturing. This allows a virtually unlimited variety of tags for use. Reverse-engineering of the tag's chemical structure from the spectrum is essentially impossible. Compared with other authentication techniques, the proposed solution is much simpler, more manageable, and widely applicable. Another significant advantage of the proposed system is that the method of applying tags to the labels or packages is an inkjet-like printing process, compatible with the barcode generation methods currently been utilized in inventory control. This extendibility and compatibility makes the adaptation of the proposed system relatively easy.

While this invention has been particularly shown and described with references to preferred embodiments thereof, it will be understood by those skilled in the art that various changes in form and details may be made therein without departing from the scope of the invention encompassed by the appended claims.

What is claimed is:

1. A Raman system comprising:
   a semiconductor tunable laser subsystem for generating a tunable signal that is tuned over a scan band of greater than 50 nanometers;
   a probe system for transmitting the tunable signal to a sample; and
   a detector system, comprising a bandpass filter for filtering a Raman signal from the sample generated by the tunable signal and a detector for detecting the filtered Raman signal.

2. A system as claimed in claim 1, wherein the semiconductor tunable laser subsystem comprises a semiconductor optical amplifier and a wavelength tunable element.

3. A system as claimed in claim 2, wherein the wavelength tunable element is integrated on a common optical bench in a common hermetic package with the semiconductor optical amplifier.

4. A system as claimed in claim 1, wherein the probe system comprises a wavelength reference detector for determining an instantaneous wavelength of the tunable signal.

5. A system as claimed in claim 1, wherein the probe system comprises an amplitude reference detector for determining amplitude of the tunable signal.

6. A system as claimed in claim 1, further comprising a controller for controlling the semiconductor tunable laser subsystem and monitoring the response of the detector to determine a Raman spectral response of the sample.

7. A system as claimed in claim 6, further comprising a housing for the Raman system and containing the semiconductor tunable laser subsystem, the probe system, the detector system, and the controller.

8. A system as claimed in claim 7, further comprising a display on the housing for providing a user interface to an operator of the system.

9. A system as claimed in claim 7, further comprising a thermoelectric cooler in the housing for controlling a temperature of the semiconductor tunable laser subsystem.

10. A system as claimed in claim 7, further comprising a thermoelectric cooler in the housing for controlling a temperature of the detector.

11. A system as claimed in claim 7, further comprising a single thermoelectric cooler for controlling a temperature of the semiconductor tunable laser subsystem and detector.

12. A system as claimed in claim 7, further comprising printed circuit board to which the semiconductor tunable laser subsystem, the probe system, the detector system, and the controller are attached.

13. A system as claimed in claim 7, further comprising a wireless interface used by the controller to transmit information to a host computer.

14. A system as claimed in claim 1, wherein the scan band is greater than 100 nanometers.

15. A system as claimed in claim 1, wherein the scan band is greater than 200 nanometers.

16. A system as claimed in claim 1, wherein the scan band is greater than 250 nanometers.

17. A method for obtaining and using a Raman response, comprising:
generating a tunable signal with a semiconductor tunable laser;
varying a wavelength of the tunable signal over a scan band of greater than 50 nanometers;
transmitting the tunable signal to a sample;
bandpass filtering a Raman signal from the sample generated by the tunable signal;
detecting the filtered Raman signal with a detector; and
analyzing the sample in response to the detector.

18. A method as claimed in claim 17, further comprising determining an instantaneous wavelength of the tunable signal.

19. A method as claimed in claim 17, further comprising determining an amplitude of the tunable signal.

20. A method as claimed in claim 17, further comprising scanning the tunable signal and monitoring the response of the detector to determine a Raman spectral response of the sample.

21. A method as claimed in claim 17, further comprising wirelessly transmitting information concerning the analysis of the sample to a host computer.

22. A method as claimed in claim 17, wherein the step of varying the wavelength comprises varying the wavelength of the tunable signal over a scan band of greater than 100 nanometers.

23. A method as claimed in claim 17, wherein the step of varying the wavelength comprises varying the wavelength of the tunable signal over a scan band of greater than 200 nanometers.

24. A method as claimed in claim 17, wherein the step of varying the wavelength comprises varying the wavelength of the tunable signal over a scan band of greater than 250 nanometers.

25. A Raman analysis system comprising:
a semiconductor tunable laser subsystem for generating a tunable signal that is tuned over a spectral scan band;
a Raman sample that generates the Raman signal from the tunable signal;
a detector system, comprising a bandpass filter for filtering a Raman signal from the Raman sample generated by the tunable signal and a detector for detecting the filtered Raman signal; and
a controller that uses the Raman signal from the Raman sample to determine an authenticity of an article with which the Raman sample is associated.

26. A system as claimed in claim 25, wherein the Raman sample is embedded in the article.

27. A system as claimed in claim 25, wherein the Raman sample is part of a bar code label of the article.

28. A system as claimed in claim 25, wherein the Raman sample is in a strip on the article.

29. A system as claimed in claim 25, wherein the Raman sample is in a dot on the article.

30. A Raman analysis system comprising:
a semiconductor tunable laser subsystem for generating a tunable signal that is tuned over a spectral scan band;
a Raman sample that generates the Raman signal from the tunable signal; and
a detector system, comprising a bandpass filter for filtering a Raman signal from the Raman sample generated by the tunable signal and a detector for detecting the filtered Raman signal; and
wherein the Raman sample is in communication with a body of a user of the system.

31. A Raman analysis system comprising:
a semiconductor tunable laser subsystem for generating a tunable signal that is tuned over a spectral scan band;
a Raman sample that generates the Raman signal from the tunable signal; and
a detector system, comprising a bandpass filter for filtering a Raman signal from the Raman sample generated by the tunable signal and a detector for detecting the filtered Raman signal; and
wherein the Raman sample is in communication with blood of a user of the system.

32. A Raman analysis system comprising:
a semiconductor tunable laser subsystem for generating a tunable signal that is tuned over a spectral scan band;
a Raman sample that generates the Raman signal from the tunable signal; and
a detector system, comprising a bandpass filter for filtering a Raman signal from the Raman sample generated by the tunable signal and a detector for detecting the filtered Raman signal; and
wherein the Raman sample is in communication with sweat of a user of the system.

33. A system as claimed in claim 25, further comprising a wireless interface for transmitting Raman information gathered from the sample to a remote host computer.

34. A Raman system comprising:
a semiconductor tunable laser subsystem for generating a tunable signal that is tuned over a scan band;
a probe system for transmitting the tunable signal to a sample; and
a detector system, comprising a bandpass filter for filtering a Raman signal from the sample generated by the tunable signal and a detector for detecting the filtered Raman signal;
a controller that is responsive to the detector system and controls the semiconductor tunable laser system to scan over subbands within the scan band at which spectral features in the Raman signal are detected by the detector system.

35. A system as claimed in claim 34, wherein the controller dithers the semiconductor tunable laser system in the subbands.

36. A system as claimed in claim 34, wherein the spectral features are peaks in the Raman signal.

37. A method for obtaining and using a Raman response, comprising:
generating a tunable signal with a semiconductor tunable laser;

varying a wavelength of the tunable signal over a scan band;
transmitting the tunable signal to a sample;
bandpass filtering a Raman signal from the sample generated by the tunable signal;
detecting the filtered Raman signal with a detector;
analyzing the sample in response to the detector;
varying the wavelength of the tunable signal over sub-bands within the scan band to detect Raman features of interest; and
generating a composite Raman signal having higher resolution spectral information for the Raman features of interest.

* * * * *